US006582901B2

United States Patent
Patterson

(10) Patent No.: US 6,582,901 B2
(45) Date of Patent: Jun. 24, 2003

(54) CELL SPECIFIC ANTI-VIRAL DRUG SUSCEPTIBILITY TEST USING TAGGED PERMISSIVE TARGET CELLS

(76) Inventor: Bruce K. Patterson, 211 W. St. Paul, Apt. 3, Chicago, IL (US) 60614

(*) Notice: Subject to any disclaimer, the term of this patent is extended or adjusted under 35 U.S.C. 154(b) by 0 days.

(21) Appl. No.: 09/843,575

(22) Filed: Apr. 26, 2001

(65) Prior Publication Data

US 2002/0012908 A1 Jan. 31, 2002

Related U.S. Application Data

(60) Provisional application No. 60/199,901, filed on Apr. 26, 2000.

(51) Int. Cl.[7] ............................. C12Q 1/70; C12Q 1/68; C12N 5/00; C12N 15/09
(52) U.S. Cl. ............................... 435/5; 435/6; 435/373; 435/69.2
(58) Field of Search ............................. 435/5, 6, 373, 435/69.2

(56) References Cited

U.S. PATENT DOCUMENTS 6,221,578 B1    4/2001   de Bethune et al. ............ 435/5
6,242,187 B1    6/2001   Capon et al. .................. 435/6

*Primary Examiner*—Hankyel T. Park
*Assistant Examiner*—Stacy S. Brown
(74) *Attorney, Agent, or Firm*—Niro, Scavone, Haller & Niro

(57) ABSTRACT

The present invention concerns a method of testing the viral susceptibility of a compound. It includes the steps of mixing subject cells infected with a virus with target cells. The target cells of the compound include a marker. Another step includes stimulating viral production. The mixture is then subjected to at least one antiviral compound. Viral production in the target cells is then detected.

19 Claims, 2 Drawing Sheets

CELL SPECIFIC ANTI-VIRAL DRUG SUSCEPTIBILITY TEST USING TAGGED PERMISSIVE TARGET CELLS

This application claims benefit of U.S. Provisional Application No. 60/199,901, filed Apr. 26, 2000.

BACKGROUND OF THE INVENTION

The advent of effective anti-viral therapies including anti viral pharmaceuticals, immune based therapies and vaccines has created a market for therapeutic susceptibility testing much like applying antibiotic disks to agar plates to test bacterial susceptibilities. Traditional patient monitoring tools such as CD4 T cell counts and viral load evaluations provide little information on the drug susceptibility patterns of HIV and other viruses. Resistance testing, specifically phenotypic testing, overcomes this barrier by helping clinicians understand exactly which drugs may or may not work for a particular patient. With this information, physicians can optimize treatment regimens for improved patient outcomes. Currently, there are two methods of drug resistance testing:

Genotyping

Genotypic resistance means that a change has occurred in the specific sequencing of nucleotides that comprise a codon. A change in a condon will lead to amino acid and structural changes in the protein, resulting in a viral mutation that can be less susceptible to antiviral medications. During genotypic analysis, the RNA or DNA fragments found in solution that correspond to genes coding for the reverse transcriptase and protease enzymes are evaluated to determine if genetic mutations are present. The results are compared to preestablished mutation patters that have shown resistance to specific antiviral drugs. If the genetic mutations present in a patient sample match the preestablished resistance mutations for a certain drug, then the virus is assumed to be resistant to that drug. Genotypic analysis is an indirect measure of drug susceptibility that offers a prediction of resistance. The results are based on averages and cannot be directly linked to treatment response.

Phenotyping

Phenotypic analysis is a direct, quantitative measure of drug resistance that does not require interpretation of complex genetic mutation patterns. Rather, phenotypic testing measures the ability of a specific viral strain to grow in vitro in the presence of a drug inhibitor. Drug susceptibility is defined by the amount of drug required to inhibit the patient virus by 50% (IC50) or 90% (IC90) as compared to a drug-sensitive reference virus. The patient virus is less susceptible to a particular drug when more of the drug is required to inhibit viral activity, versus the amount of drug required to inhibit the reference virus.

Because the virus is directly exposed to each of the available antiretroviral medications, results can be directly linked to treatment response. For example, if the patient virus shows resistance to a particular drug, that drug can be avoided or omitted from the patient's treatment regimen, allowing the physician to design a treatment plan that is more likely to be effective for a longer period of time.

SUMMARY OF THE PRESENT INVENTION

Currently available genotyping assays require gene sequencing to detect resistance mutations. Currently available phenotyping assay require cloning of the patients isolate into either specialized vectors (Virologic) or cells (Virco) and subsequent exposure to the drugs to be tested. Both genotyping and phenotyping can take up to two (2) weeks for the results because of the labor and analysis required (genotyping) or long culture times because of the insensitivity of the detection system (p24 antigen). Further, all genotyping and phenotyping assays assume that resistance is inherent in the virus, in particular, in the gene sequence of the virus.

The present invention provides a technique that addresses the fact that viral resistance may be a function of the cell types infected and the point at which the antiviral compound inhibits viral replication in the lifecycle of the virus within these cell types. The present invention can detect if viral resistance is due to the fact that viruses may not proceed through a normal lifecycle in certain cells, such as monocytes or dendritic cells. The present invention does this by mixing virally infected subject cells with tagged target cells having a marker. Viral production is then stimulated and the mixture is subjected to an antiviral compound. The mixture is then analyzed for viral production in the target cells.

DESCRIPTION OF THE DRAWINGS

These and other features, objects and advantages of the present invention will become apparent from the following description and drawings wherein like reference numerals represent like elements in several views, and which.

DESCRIPTION OF THE PREFERRED EMBODIMENT

Set forth below is a description of what are currently believed to be the preferred embodiments or best examples of the invention claimed. Future and present alternatives and modifications to the preferred embodiments are contemplated. Any alternates or modifications in which insubstantial changes in function, in purpose, in structure or in result are intended to be covered by the claims of this patent.

Several methods have been developed to determine viral resistance to anti-viral and anti-retroviral drugs. These methods either involve the detection of genetic mutations in the genes responsible for resistance or use nucleic acid amplification to derive HIV protease (PR) and reverse transcriptase (RT) sequences from a patient plasma sample. Both these approaches are time consuming (requiring at least fourteen days for an answer), labor intensive, costly and test for the presence of viral replication in solution. Moreover, these methods require the cloning of the virus or viral genes.

Figure 1:
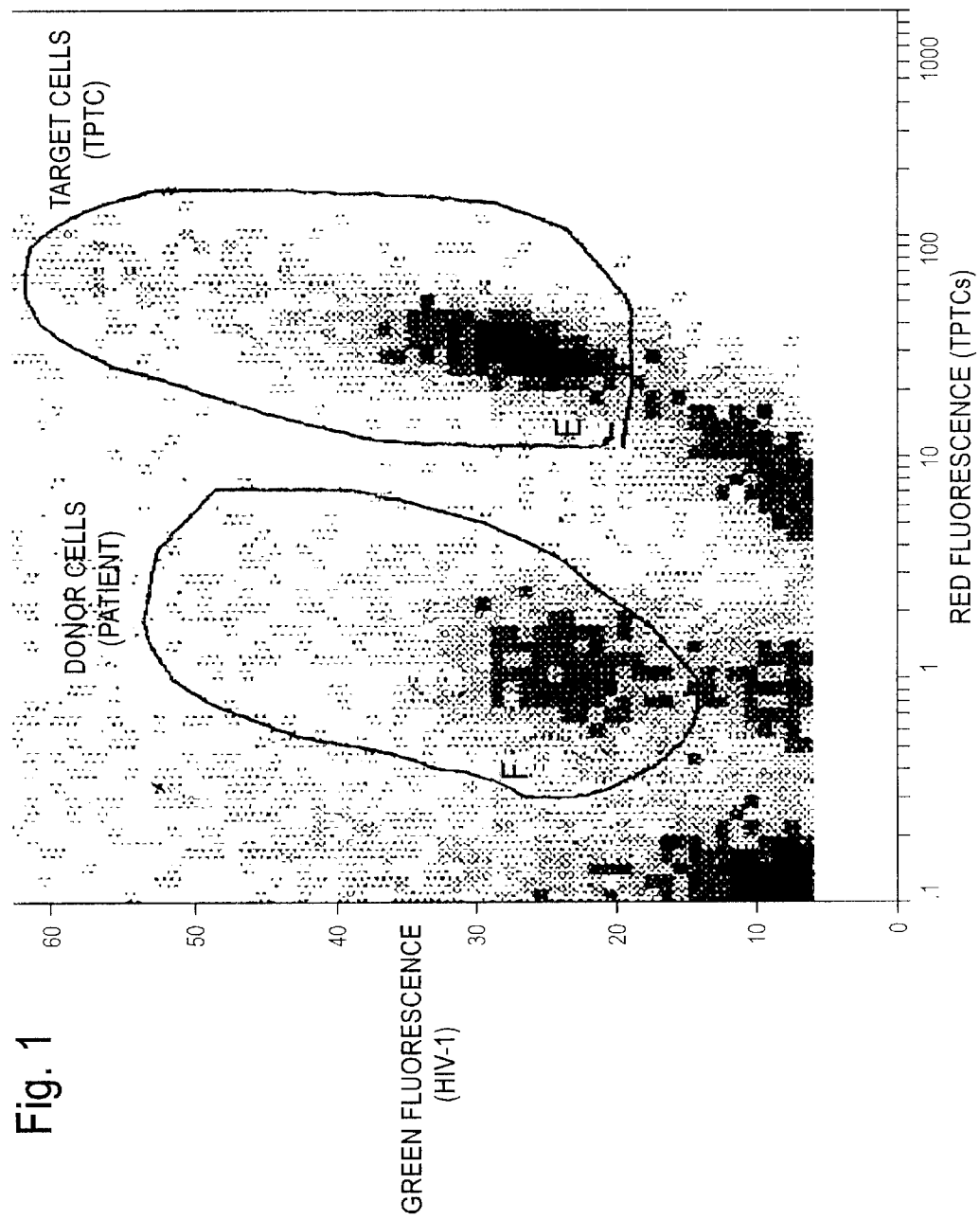
FIG. 1 shows separation between target cells and subject cells prior to subjecting the cell mixture to an antiviral compound.
Figure 2:
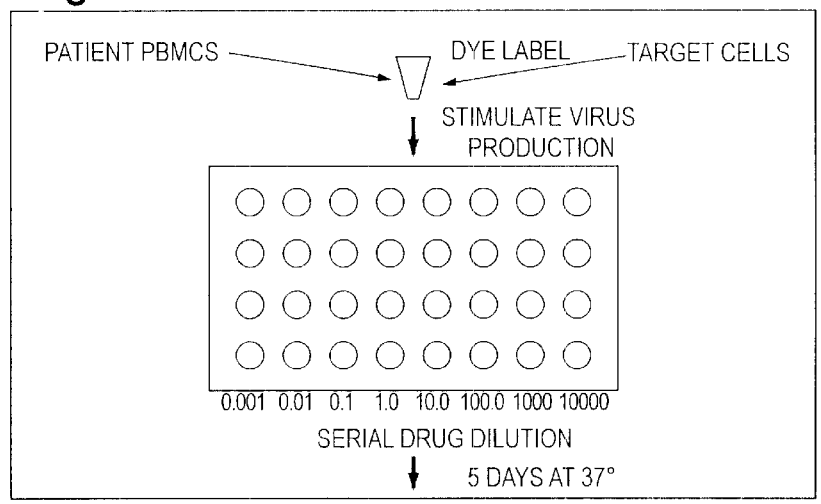
FIG. 2 is a flow diagram of one embodiment of the present invention.

The present invention overcomes these limitations. As shown in FIGS. 1 and 2 in one embodiment of the present invention, the time to conduct the test may be reduced to about five days. The method is based on the ability of a virus to infect target cells. The target cells are tagged or marked in such a manner to distinguish the target cells from infected input or subject cells from the patient sample. One way in which this may be done is by fluorescently labeling the target cells with a non-transferable dye. Other means known to those of skill in the art may be used, including, but not limited to, colometric dyes, chemiluminescent dyes, and radioactive markers.

Figure 3:
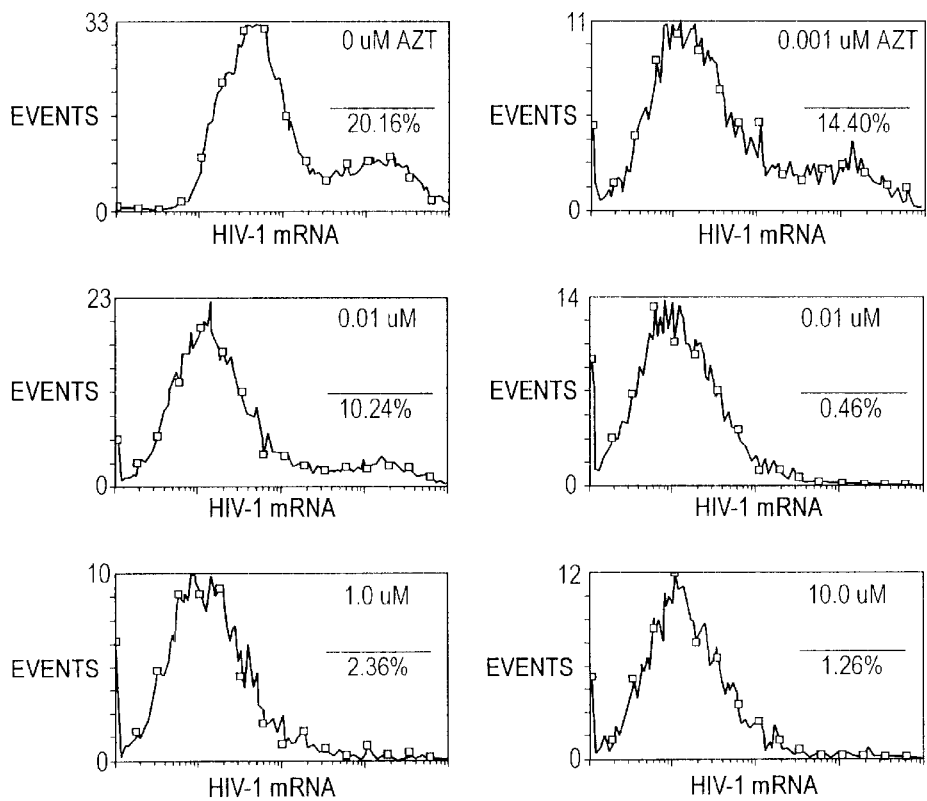
FIG. 3 is a determination of viral susceptibility to a compound.

Next, the patient sample and the tagged cells are placed in culture with compounds that stimulate viral production. In multiple test wells, which may be a serial dilution or a serial dilution of multiple concentrations, different doses of anti-viral or anti-retroviral drugs are included in the culture media. FIG. 3 shows how AZT was used as a test compound in connection with HIV and subject to serial dilution. Infected target cells are quantified by flow cytometry using fluorescence in situ hybridization to detect the virus within the cells. Two-color analysis allows for the detection of the fluorescent-tagged target cells and virally-infected cells simultaneously. A dose response curve can be generated based on the inhibition of infection by the anti-viral or anti-retroviral drug and results will be reported as the 50% of 90% inhibitory dose of drug. Of course, other methods known to those of skill in the art may be used including, but not limited to, in-situ hydridization, polymerase chain reaction, nucleic acid hybridization, hybrid capture, and branched DNA detection as well as through other methods.

This co-culture method combines the ease of a culture-based assay system with a highly sensitive detection method. Whereas other methods require extensive manipulation of the virus and/or viral nucleic acids, this method requires only the isolation of patients' blood cells prior to co-culture. In contrast with phenotyping or genotyping, which are labor intensive and expensive methods of detecting mutations associated with drug resistance, this method provides a direct measurement of drug susceptibility based on viral growth characteristics. The methods described above would be useful in testing such compounds as entry inhibitors, nucleoside inhibitors, non-nucleoside inhibitors, integrase inhibitors, protease inhibitors, transcription inhibitors as well. This is so because the invention does not analyze a solution containing the viral matter. Instead, the use of a target cell takes into account that the viral lifecycle may not be the same in all human cells (e.g., HIV in macrophages). Moreover, by examining the viral resistance at a cellular level, instead of in a solution, the present invention is able to analyze susceptability even though a compound may act to inhibit viral replication at a specific stage in a normal viral lifecycle.

While the preferred embodiments of the present invention have been illustrated and described, it will be understood by those of ordinary skill in the art that changes and other modifications can be made without departing from the invention in its broader aspects. Various features of the present invention are set forth in the following claims.

What is claimed is:

1. A method of screening at least one anti-viral compound comprising:

mixing virally infected subject cells with target cells;

said target cells having a marker;

subjecting said mixture to at least one antiviral compound;

stimulating viral production;

detecting viral production in said target cells.

2. The method of claim 1 wherein said detection is performed by in-situ hybridization.

3. The method of claim 1 wherein said detection is performed by polymerase chain reaction.

4. The method of claim 1 wherein said detection is performed by nucleic acid hybridization.

5. The method of claim 1 wherein said detection is performed by hybrid capture.

6. The method of claim 1 wherein said detection is performed by b ranched DNA detection.

7. The method of claim 1 wherein said marker is a dye.

8. The method of claim 7 wherein said dye is non-transferable.

9. The method of claim 1 wherein said marker is a fluorescent dye.

10. The method of claim 1 wherein said marker is a colorimetric dye.

11. The method of claim 1 wherein said marker is a chemiluminescent dye.

12. The method of claim 1 wherein said target cell is susceptible to the same virus that infects said subject cells.

13. The method of claim 1 wherein said compound is an entry inhibitor.

14. The method of claim 1 wherein said compound is a nucleoside inhibitor.

15. The method of claim 1 wherein said compound is a non-nucleoside inhibitor.

16. The method of claim 1 wherein said compound is an integrase inhibitor.

17. The method of claim 1 wherein said compound is a polymerase inhibitor.

18. The method of claim 1 wherein said compound is a protease inhibitor.

19. The method of claim 1 wherein said compound is a transcription inhibitor.

* * * * *